(12) United States Patent
Sawicz

(10) Patent No.: US 10,893,978 B2
(45) Date of Patent: Jan. 19, 2021

(54) VITREOUS CUTTER PNEUMATIC DRIVER

(71) Applicant: Novartis AG, Basel (CH)

(72) Inventor: Conrad Sawicz, Lake Forest, CA (US)

(73) Assignee: Alcon Inc., Fribourg (CH)

( * ) Notice: Subject to any disclaimer, the term of this patent is extended or adjusted under 35 U.S.C. 154(b) by 211 days.

(21) Appl. No.: 16/211,400

(22) Filed: Dec. 6, 2018

(65) Prior Publication Data

US 2019/0183679 A1 Jun. 20, 2019

Related U.S. Application Data

(60) Provisional application No. 62/598,642, filed on Dec. 14, 2017.

(51) Int. Cl.
| | | |
|---|---|---|
| *A61F 9/007* | (2006.01) | |
| *A61B 17/00* | (2006.01) | |
| *A61B 17/32* | (2006.01) | |
| *A61F 9/008* | (2006.01) | |

(52) U.S. Cl.
CPC .......... *A61F 9/00736* (2013.01); *A61B 17/00* (2013.01); *A61B 17/32* (2013.01); *A61F 9/00763* (2013.01); *A61B 2017/00017* (2013.01); *A61B 2017/00544* (2013.01); *A61B 2017/320028* (2013.01); *A61F 2009/00874* (2013.01)

(58) Field of Classification Search
CPC .............. A61F 9/00736; A61F 9/00763; A61F 2009/00874; A61B 17/00; A61B 17/1628; A61B 17/32; A61B 2017/00017; A61B 2017/00535; A61B 2017/00544; A61B 2017/320028; A61B 5/150167; A61B 2018/00934

See application file for complete search history.

(56) References Cited

U.S. PATENT DOCUMENTS

| | | | |
|---|---|---|---|
| 4,696,298 | A | 9/1987 | Higgins |
| 5,176,628 | A | 1/1993 | Charles |
| 5,403,276 | A * | 4/1995 | Schechter .......... A61B 18/1482 604/22 |
| 6,258,111 | B1 * | 7/2001 | Ross ................ A61B 17/32002 606/171 |
| 6,575,990 | B1 | 6/2003 | Wang |
| 6,743,245 | B2 | 6/2004 | Lobdell |
| 8,038,692 | B2 | 10/2011 | Valencia |
| 8,080,029 | B2 | 12/2011 | Charles |
| 8,187,293 | B2 | 5/2012 | Kirchhevel |
| 8,298,253 | B2 | 10/2012 | Charles |
| 8,312,800 | B2 * | 11/2012 | Turner ................ A61F 9/00736 83/639.1 |
| 8,540,743 | B2 | 9/2013 | Auld |
| 8,821,524 | B2 | 9/2014 | Agahi |
| 8,888,802 | B2 | 11/2014 | Underwood |
| 9,095,409 | B2 | 8/2015 | Underwood |

(Continued)

FOREIGN PATENT DOCUMENTS

CN 101829790 B 8/2011

*Primary Examiner* — Ashley L Fishback

(57) ABSTRACT

Systems and methods for driving the cutter of a vitrectomy handpiece using a substantially hermetically sealed system having a pneumatic pump for alternatively creating both positive pressure for pushing a first side of a diaphragm in the vitreous cutter and pulling negative pressure to pull the other side of the diagram, and vice versa.

15 Claims, 12 Drawing Sheets

(56) References Cited

U.S. PATENT DOCUMENTS

| | | |
|---|---|---|
| 9,101,441 B2 | 8/2015 | Underwood |
| 9,486,360 B2 | 11/2016 | Chon |
| 9,517,161 B2 | 12/2016 | Underwood |
| 9,757,273 B2 | 9/2017 | Heeren |
| 9,974,689 B2 | 5/2018 | Mcdonell |
| 10,251,782 B2 | 4/2019 | Farley |
| 10,555,834 B2 | 2/2020 | Charles |
| 2007/0185514 A1 | 8/2007 | Kirchhevel |
| 2008/0154292 A1 | 6/2008 | Huculak |
| 2008/0188881 A1 | 8/2008 | Chon |
| 2009/0259242 A1* | 10/2009 | Gerg ................ A61F 9/00736 606/167 |
| 2013/0144317 A1 | 6/2013 | Valencia |
| 2016/0120697 A1 | 5/2016 | Farley |
| 2017/0027753 A1 | 2/2017 | De Santis |
| 2017/0333252 A1 | 11/2017 | Biancalana |
| 2018/0243134 A1 | 8/2018 | Dean |
| 2018/0369016 A1 | 12/2018 | Underwood |
| 2019/0000672 A1 | 1/2019 | Mcdonell |
| 2019/0099292 A1* | 4/2019 | Strayer ................ A61B 34/25 |

\* cited by examiner

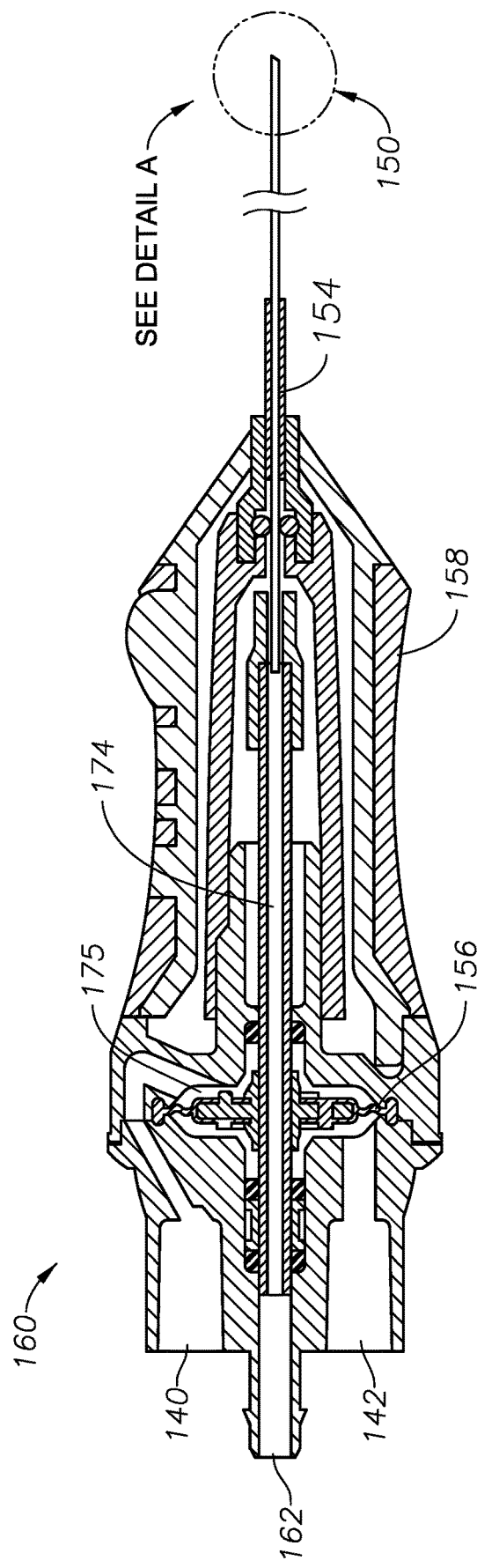
FIG. 3
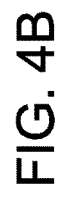
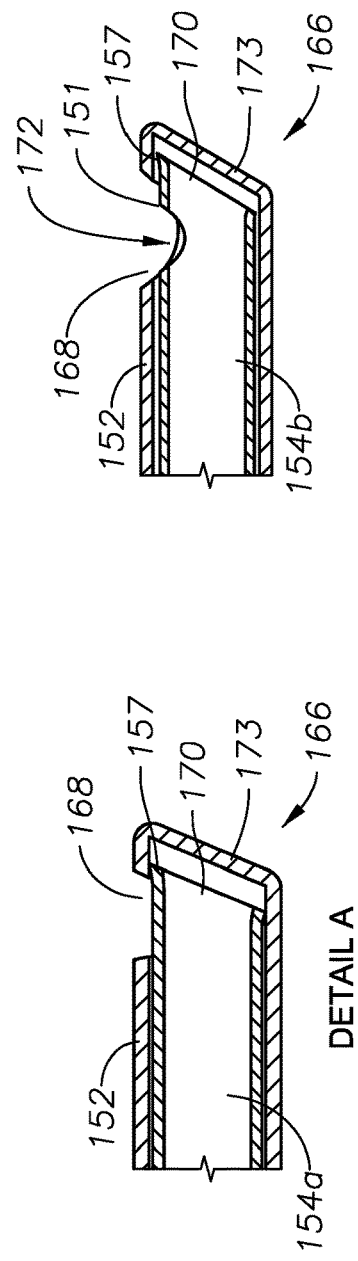
FIG. 4A
FIG. 4B

VITREOUS CUTTER PNEUMATIC DRIVER

PRIORITY CLAIM

This application claims the benefit of priority of U.S. Provisional Patent Application Ser. No. 62/598,642 titled "VITREOUS CUTTER PNEUMATIC DRIVER", filed on Dec. 14, 2017, whose inventor is Conrad Sawicz, which is hereby incorporated by reference in its entirety as though fully and completely set forth herein.

BACKGROUND

Field of the Disclosure

The present disclosure relates to systems for driving the cutter of a vitrectomy handpiece and more specifically to a substantially hermetically sealed system having a pneumatic pump for alternatively creating both positive pressure for pushing a first side of a diaphragm in the vitreous cutter and pulling negative pressure to pull the other side of the diagram, and vice versa.

Description of Related Art

In many ophthalmic procedures a surgeon is required to use a variety of instruments in the patient's eye. For example, in a vitrectomy, a pneumatic driver can drive a cutter in a handpiece to cut and aspirate vitreous from a patient's eye. Some ophthalmic surgical systems use a pneumatic driver that alternatively delivers pneumatic pressure two ports of a surgical handpiece and then vents the ports to atmosphere. Since this system is vented, it is an open system and needs a continuous flow of air. Also, in this open system, a pneumatic valve is connected to a pressure source and when the valve opens, the pressure increases in the pneumatic hose connected to the vitreous cutter. The rate of pressure increase is a function of the mechanical design of the pneumatic valve. The maximum pressure in the hose is controlled by the pressure source. To remove pressure the pneumatic valve is closed, and a second valve is opened to vent the system. Additionally, the pneumatic connection between the vitreous cutter and the pressure source can be made with a pair compliant flexible hoses which allow free motion of the vitreous cutter to facilitate surgery. In an open system, the use of a compliant hose results in the pressure increase at the distal end of the tubing to be relatively slow because the internal volume of the hose increases with applied pressure. This can delay the motion of the vitreous cutter diaphragm and is one of the limitations of the cycle rate of the vitreous cutter.

SUMMARY

The technology described below involves systems and methods for driving the cutter of a vitrectomy handpiece and more specifically to a substantially hermetically sealed system having a pneumatic pump for alternatively creating both positive pressure for pushing a first side of a diaphragm in the vitreous cutter and pulling negative pressure to pull the other side of the diagram, and vice versa.

Some embodiments of the present technology can involve a pneumatic driver for push/pull driving of a diaphragm in an ophthalmic surgical handpiece. The pneumatic driver can involve a voice coil driver including a voice coil and a shaft driven by the voice coil and a pair of pneumatic pumps. The pair of pneumatic pumps can include: a master pneumatic pump positioned on a first side of the voice coil driver and a replica pneumatic pump positioned coaxially with the master pneumatic pump on a second side of the voice coil driver. Each of the master pneumatic pump and replica pneumatic pump can have a substantially hermetically sealed outer body, an outlet, and an internal pump coupled with a driving arm coupled with the shaft of the voice coil driver.

In some embodiments, a motion of the shaft in a first direction produces positive pressure by the master pneumatic pump and pulls negative pressure in the replica pneumatic pump. Likewise, a motion of the shaft in a second direction produces positive pressure by the replica pneumatic pump and pulls negative pressure in the master pneumatic pump. The pneumatic driver can also include an amplifier for providing a current to the voice coil driver for driving the shaft back and forth in the first and the second direction.

Some embodiments of the present technology, also involve a vitrectomy handpiece having a housing containing an inner cutting tube at least partially contained within an outer cutting tube and coupled with a pneumatic driver diaphragm. A first side of the pneumatic driver diaphragm can be in fluid communication with a first air port and a second side of the pneumatic driver diaphragm is in fluid communication with a second air port. The vitrectomy handpiece can be coupled with a pneumatic driver for push/pull driving via a pair of tubings respectively coupling the outlet tube port of the first pneumatic diaphragm pump with the first air port of the vitrectomy handpiece and the outlet tube port of the second pneumatic diaphragm pump with the second air port of the vitrectomy handpiece. In these cases, positive pneumatic pressure from the master pneumatic pump and the negative pressure from the replica pneumatic pump simultaneously pushes the first side of the pneumatic driver diaphragm while driving the inner cutting tube forward within the outer cutting tube. Likewise, positive pneumatic pressure from the replica pneumatic pump and the negative pressure from the master pneumatic pump simultaneously pushes the second side of the pneumatic driver diaphragm while driving the inner cutting tube back within the outer cutting tube.

In some cases, the internal pump of the master pneumatic pump and the replica pneumatic pump comprises a pump diaphragm ranging between two and five times the size of the diaphragm in an ophthalmic surgical handpiece. In some cases, the internal pump of the master pneumatic pump and the replica pneumatic pump comprises a pneumatic piston having a piston ring coupled to the driving arm. In some cases, the master pneumatic pump and the replica pneumatic pump produce and pull a pressure between five and fifteen pounds per square inch at a distal end of each respective tubing.

Some embodiments of the present technology also involve pressure sensor feedback control system including a pressure sensor configured to detect a pressure in one or more of the master pneumatic pump, the replica pneumatic pump, the tubings, the first air port, and the second air port. The pressure sensor feedback control system can also include a controller that can adjust the current in the amplifier to adjust the pressure in one or more of the master pneumatic pump, the replica pneumatic pump, the tubings, the first air port, and the second air port.

Some embodiments of the present technology include a method of driving a vitrectomy cutter. The method can include assembling a voice coil with a shaft that is driven with a current back and forth between a first side and a second side of the voice coil, coupling a first end of the shaft to a first pneumatic pump, coupling a second end of the shaft to a second pneumatic pump, coupling an outlet port of the first pneumatic pump with a first air port of vitrectomy handpiece, wherein the first air port of the vitrectomy handpiece is in fluid communication with a first side of a diaphragm for pushing the cutter of the vitrectomy handpiece, and coupling an outlet port of the second pneumatic pump with a second air port of the vitrectomy handpiece, wherein the second air port of the vitrectomy handpiece is in fluid communication with a second side of the diaphragm for pulling the cutter of the vitrectomy handpiece. The method can further include supplying the voice coil with a current for driving the shaft back and forth, thereby alternatively: simultaneously producing positive pneumatic pressure from the first pneumatic pump and producing negative pressure from the second pneumatic pump to simultaneously push the first side of the pneumatic driver diaphragm to drive the cutter forward; and simultaneously producing negative pneumatic pressure from the first pneumatic pump and producing positive pressure from the second pneumatic pump to simultaneously push the second side of the pneumatic driver diaphragm to drive the cutter back.

In some cases, the method can additionally include fluidly coupling a pressure sensor to one or more of the master pneumatic pump, the replica pneumatic pump, the tubings, the first air port, and the second air port; detecting a pressure in the one or more of the master pneumatic pump, the replica pneumatic pump, the tubings, the first air port, and the second air port; and adjusting the current in the amplifier to adjust the detected pressure in the one or more of the master pneumatic pump, the replica pneumatic pump, the tubings, the first air port, and the second air port.

BRIEF DESCRIPTION OF THE DRAWINGS

For a more complete understanding of the present technology, its features, and its advantages, reference is made to the following description, taken in conjunction with the accompanying drawings, in which:

FIG. 3 shows a partial cross-sectional illustration of a vitrectomy probe;

FIGS. 4A-4B illustrate a distal end of the vitrectomy probe with an inner cutting tube;

DESCRIPTION

The technology described herein involves systems for driving the cutter of a vitrectomy handpiece and more specifically to a substantially hermetically sealed system having a pneumatic pump for alternatively creating both positive pressure for pushing a first side of a diaphragm in the vitreous cutter and pulling negative pressure to pull the other side of the diagram, and vice versa.

Figure 1:
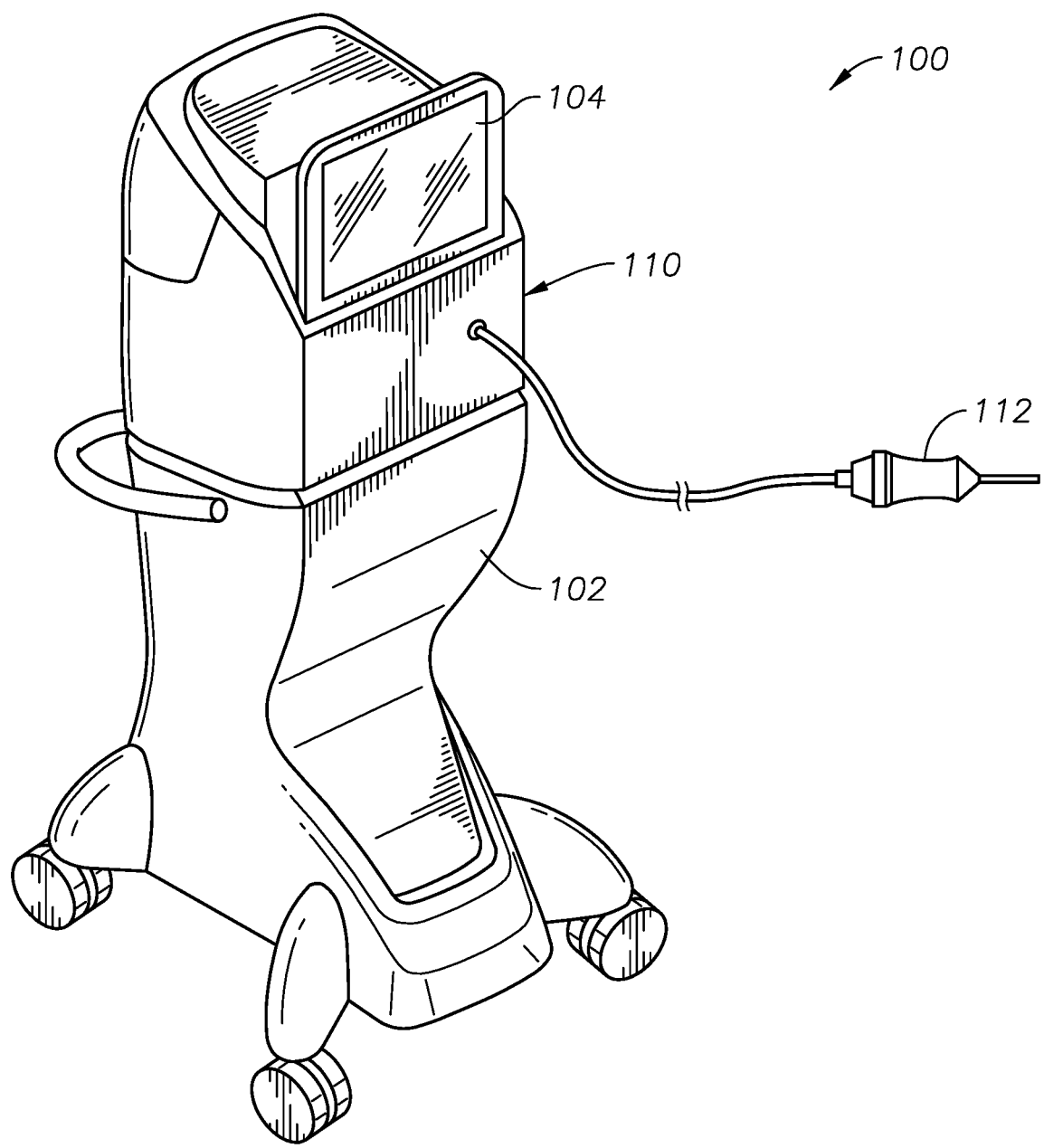
FIG. 1 illustrates a vitrectomy surgical system console.

FIG. 1 illustrates a vitrectomy surgical system console, generally designated 100, according to an exemplary embodiment. The surgical console 100 may include a base housing 102 and an associated display screen 104 showing data relating to system operation and performance during a vitrectomy surgical procedure. The surgical console 100 may include a vitrectomy probe system 110 that includes a vitrectomy probe 112, as will be discussed in more detail below with respect to subsequent figures.

Figure 2:
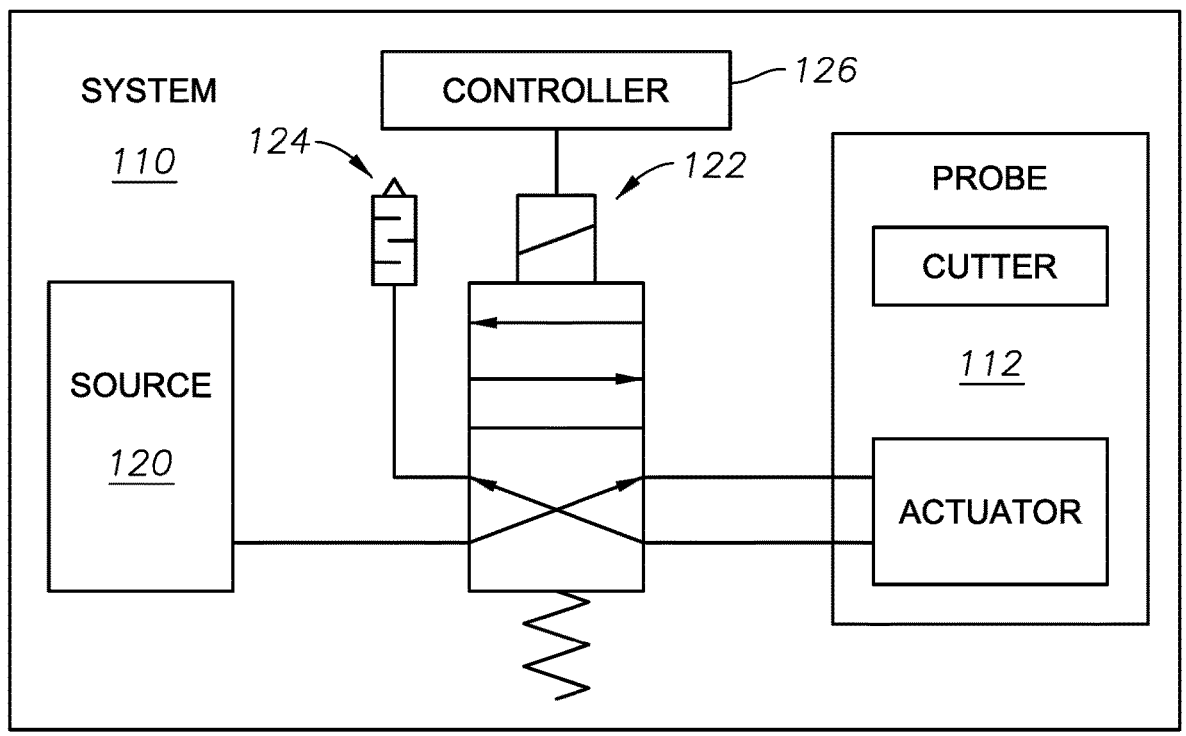
FIG. 2 is a schematic of a vitrectomy probe system using an on/off pneumatic driver.

FIG. 2 is a schematic of a vitrectomy probe system 110 using an on/off pneumatic driver. The probe system 110 may include the vitrectomy probe 112, a pneumatic pressure source 120, a probe driver shown as an adjustable directional on-off pneumatic driver 122, a muffler 124, and a controller 126. In an embodiment, the controller 126 may be a processor that includes one or more processing cores capable of performing parallel or sequential operations. Alternatively, the controller 126 may be a dedicated piece of hardware such as an application specific integrated circuit (ASIC), to name just a few examples. The source 120, the driver 122, the muffler 124, and the probe 112 may be in fluid communication with each other along lines representing flow paths or flow lines. The controller 126 may be in electrical communication with the driver 122. In an embodiment, the controller 126 may control operation of both the driver 122 and various aspects of the probe 112, including the frequency of oscillation by way of the actuator as well as a flow rate of fluid to/from the surgical site.

FIG. 3 shows a partial cross-sectional illustration of a vitrectomy probe 112. In this example, the vitrectomy probe 112 may be a pneumatically driven probe that operates by receiving pneumatic pressure alternating through first and second ports 140 and 142. The probe 112 may include as its basic components a cutter 150 has an outer cutting tube 152 (also known as a needle), an inner cutting tube 154 shown in a non-sectional side view, and a probe actuator or motor shown here as a reciprocating air driven diaphragm 156, all at least partially encased by a housing 158 in an enclosed drive chamber 175. The housing 158 may include an end piece 160 at the probe proximal end with the first and second air supply ports 140, 142 and one suction port 162 to provide aspiration of materials from the cutter 150.

In an embodiment, the vitrectomy probe system's pneumatic driver 122 (FIG. 2) may be a standard four-way on-off valve. The pneumatic driver 122 may have a solenoid that operates to move the driver to one of the two on-off positions depicted in the example of FIG. 2. Here, the pneumatic driver 122 may be in a position to provide pneumatic pressure to the first port 140 (FIG. 3), and to vent pneumatic pressure from the second port 142 (FIG. 3). In this position, pneumatic pressure may pass from the pressure source 120, through the on-off pneumatic driver 122, and to the first port 140 where the pneumatic pressure provides pneumatic power to the vitrectomy probe 112. At the same time, pneumatic pressure at the second port 142 may pass through the on-off pneumatic driver 122 to the muffler 124 where it is exhausted, for example, to the atmosphere. In the other position, the on-off pneumatic driver 122 may allow pneumatic pressure to pass from the pressure source 120 to the second port 142, where the pneumatic pressure provides pneumatic power to the vitrectomy probe 112. At the same time, pneumatic pressure at the first port 140 may vent through the on-off pneumatic driver 122 to the muffler 124 where it is exhausted to the atmosphere. The on-off pneumatic driver may be configured to receive operating signals from the controller 126.

In operation, pneumatic pressure may be directed alternately from the source 120 to the first and second ports 140, 142 to operate the vitrectomy probe 112. The on-off pneumatic driver 122 may alternate between its two positions very rapidly to alternatingly provide pneumatic pressure to the first and second ports 140, 142. Although shown with a single pneumatic driver 122, other embodiments include two pneumatic drivers, one associated with each of the two ports 140, 142. These embodiments may operate similar to the manner described, with the drivers being configured to independently receive operating signals from the controller 126 (FIG. 2). Yet other arrangements are contemplated.

Returning to FIG. 3, the cutter 150 may extend from the housing 158 and may include a distal end 166, shown in FIG. 4a in greater detail below. The outer cutting tube 152 and the inner cutting tube 154 may both be cylindrical tubes with a hollow bore. As seen in FIGS. 4a-b, the distal ends (needle caps 173) of the outer cutting tube 152 may include beveled (i.e., angled) ends. In some embodiments, the distal ends (needle caps 173) of the outer cutting tubes may be flat. The distal ends of the outer cutting tube 152 may be closed using, for example, spin closed machining, adhesive, welding (e.g., laser welding), etc. For example, the beveled end may be closed by laser welding a pieced onto the angled end. In some embodiments, the inner cutting tube 154 may additionally have an open end, such as depicted in FIGS. 4a-b as a distal port 170.

Generally, the inner cutting tube 154 may oscillate within the outer cutting tube 152 in response to the probe actuator. In an embodiment, the inner cutting tube 154 may be driven by air pressure directed on opposing sides of the diaphragm 156. In one example of operation, if air pressure is increased at the first port 140, the diaphragm 156 may move distally, displacing the inner cutting tube 154 relative to the outer cutting tube 152, thereby moving a first cutting edge 157 on a distal end of the inner cutting tube 154 in the distal direction and cutting tissue. This may cut any vitreous material which may have been aspirated into a tissue-receiving outer port 168 of the outer cutting tube 152.

In some embodiments, the first cutting edge 157 may be formed on a flared distal end of the inner cutting tube 154 (as illustrated in FIGS. 4A-4B). In some embodiments, the distal end of the inner cutting tube 154 may not be flared. The vitreous may be aspirated through a distal opening 170 of the inner cutting tube 154. In some embodiments, the vitreous may also be aspirated through distal port 172 in the side of inner cutting tube 154b. "154a" used in the Figures to depict inner cutting tube with no side distal port 172, and "154b" used in the Figures to depict inner cutting tube with a side distal port 172 ("154a" and "154b" are generally referred to as "154" in the drawings and the specification when the expressed detail may apply to both "154a" and "154b"). Venting the pressure at the 5 first port 140 and increasing the pressure at the second port 142 may move the diaphragm 156 proximally, moving a second cutting edge 151 facing a proximal direction near the distal end of the inner cutting tube 154b in the proximal direction, cutting any vitreous material which may have entered the outer port 168 of the outer cutting tube 152 and the side distal port 172 of the inner cutting tube 154b while at least partially aligned.

As explained herein, the pneumatic driver 122 described in FIG. 2 is an on/off pneumatic driver that alternatively delivers pneumatic pressure to the first and second ports 140, 142 and then venting the ports to atmosphere. Since this system is vented, it is an open system and needs a continuous flow of air. Also, in this open system, a pneumatic valve is connected to a pressure source and when the valve opens, the pressure increases in the pneumatic hose connected to the vitreous cutter. The rate of pressure increase is a function of the mechanical design of the pneumatic valve. The maximum pressure in the hose is controlled by the pressure source. To remove pressure the pneumatic valve is closed, and a second valve is opened to vent the system. Additionally, the pneumatic connection between the vitreous cutter and the pressure source can be made with a pair compliant flexible hoses which allow free motion of the vitreous cutter to facilitate surgery. In an open system, the use of a compliant hose results in the pressure increase at the distal end of the tubing to be relatively slow because the internal volume of the hose increases with applied pressure. This can delay the motion of the vitreous cutter diaphragm and is one of the limitations of the cycle rate of the vitreous cutter.

Some embodiments of the present technology involve a closed system having a pneumatic pump driving the vitreous cutter. The pneumatic driver in a closed system can create both positive pressure for pushing a diaphragm in the vitreous cutter and can pull negative pressure.

Figure 5A:
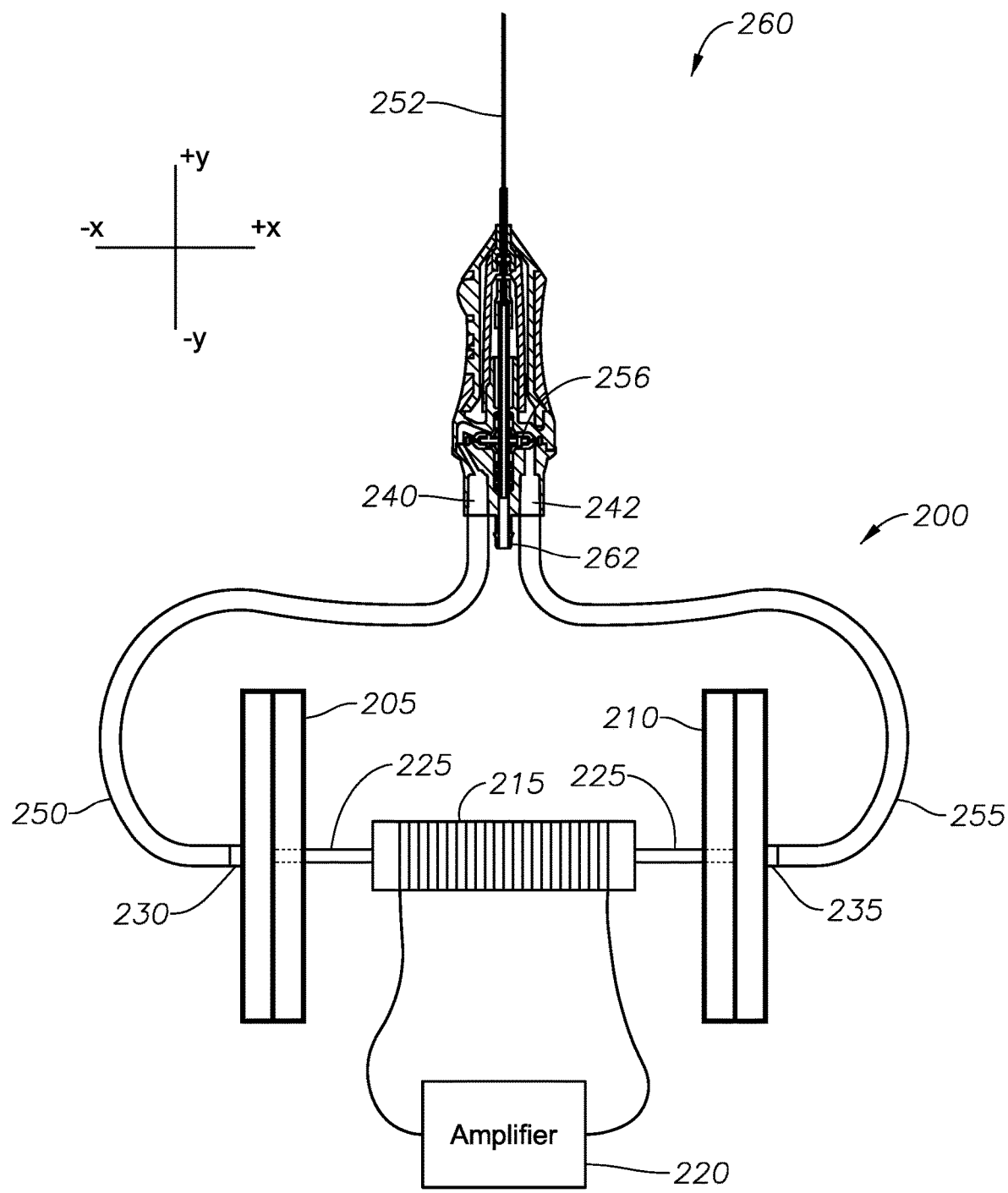
FIG. 5A illustrates a diaphragm pump driver system with a pair of diaphragm pumps, a voice coil, and an amplifier according to some embodiments of the present technology.

FIG. 5A illustrates a diaphragm pump driver system 200 with a pair of diaphragm pumps 205, 210 and a voice coil 215 and an amplifier 220. The voice coil 215 can include a shaft 225 coupled with each of the diaphragm pumps 205, 210. The amplifier 220 can drive the voice coil 215 with an alternating current, causing the shaft 225 to move back and forth and alternatively pumping one of the diaphragm pumps 205, 210 to create positive pressure and pulling the other diaphragm pump 205, 210 to pull negative pressure. The diaphragm pumps 205, 210 can each include an outlet 230, 235 for coupling with an air hose 250, 255 and the ports 240, 242 of a hand piece 260. The ports 240, 242 of the hand piece 260 each communicate fluid pressure to one side of pneumatic driver diaphragm 256 which drives the inner cutting tube within an outer cutting tube 252. The hand piece can also include a suction port 262 to provide aspiration of materials from the cutter through an additional tube (not shown).

The air hose 250, 255 connections with the outlets 230, 235 and with the ports 240, 242 can be substantially hermetically sealed. Also, the interface between the shaft 225 and the walls of the diaphragm pumps 205, 210 can be substantially hermetically sealed. Therefore, the diaphragm pump driver system 200 can be a closed system.

In a closed system with voice coil 215 actuated diaphragm pumps 205, 210, the pressure increase is controlled by the size of the diaphragms 205, 210, and the stroke of the voice coil 215. The amount of pressure created is proportional to the volume change achieve by the diaphragms' 205, 210 motion. The pressure can be held constant by holding the diaphragm still. So, an arbitrary pressure profile can be created, including negative pressure, by controlling the electrical drive waveform. For example, the motion of the voice coil 215 can create a linear ramp, a square wave, an exponential/logarithmic wave, etc.

Figure 5B:
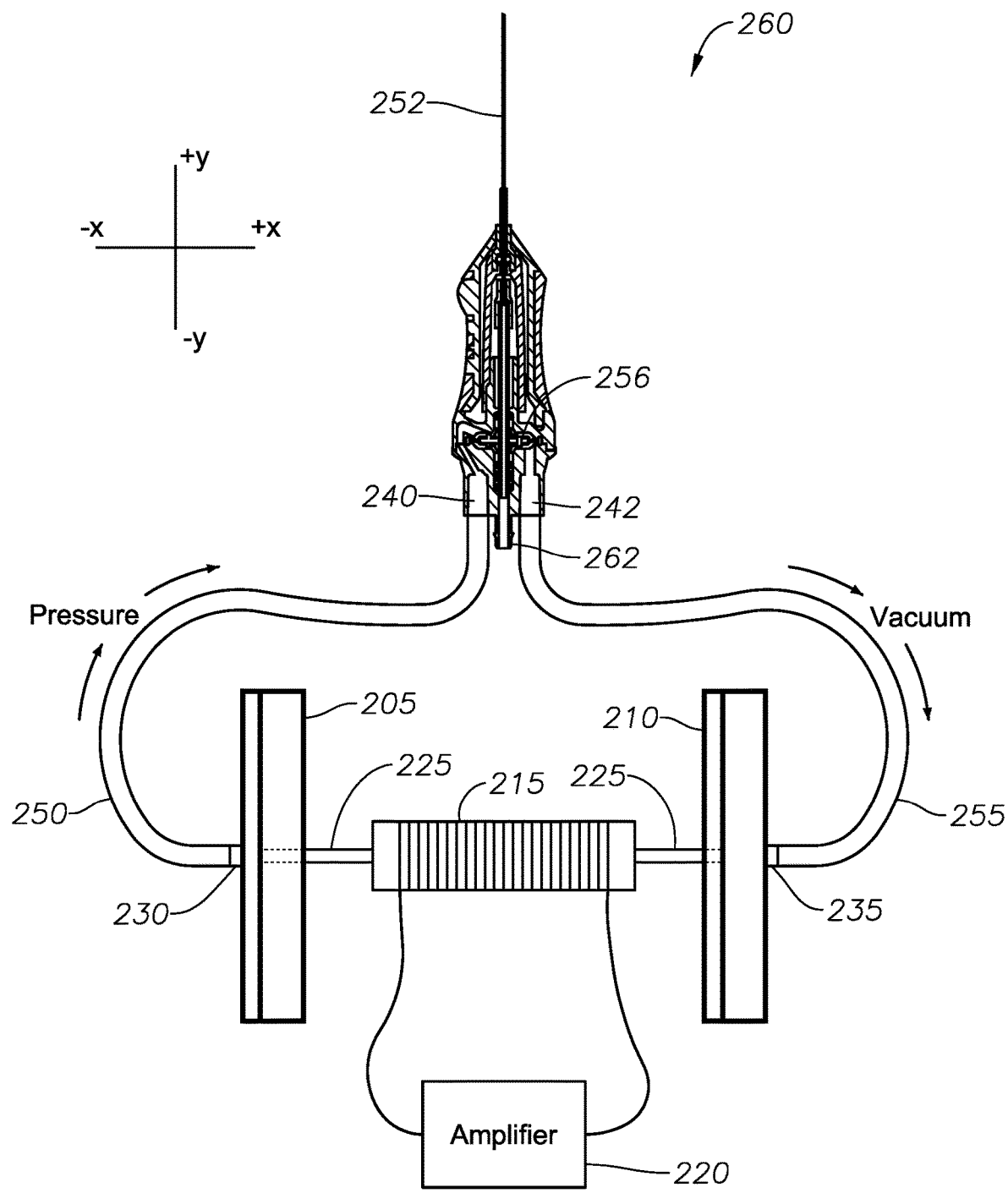
FIG. 5B illustrates a first portion of the pump cycle of a diaphragm pump driver system.

The diaphragm pump driver system 200 can use the pair of diaphragm pumps 205, 210 to drive the vitreous cutter 252. FIG. 5B illustrates a first portion of the pump cycle of the diaphragm pump driver system 200. In the first half of the pump cycle, the amplifier 220 provides a current that causes the voice coil 215 to drive the shaft 225 and the diaphragm pump 205 in the −x direction, thereby pushing pressure through the air hose 250 and causing a positive displacement (+y) of the vitreous cutter diaphragm 256. The displacement of the shaft 225 in the −x direction will also pull the diaphragm pump 210, thereby pulling a vacuum in air hose 255 and further causing positive displacement (+y) of the vitreous cutter diaphragm 256 since the port 242 is in fluid communication with the opposite (+y) side of the vitreous cutter diaphragm 256.

Figure 5C:
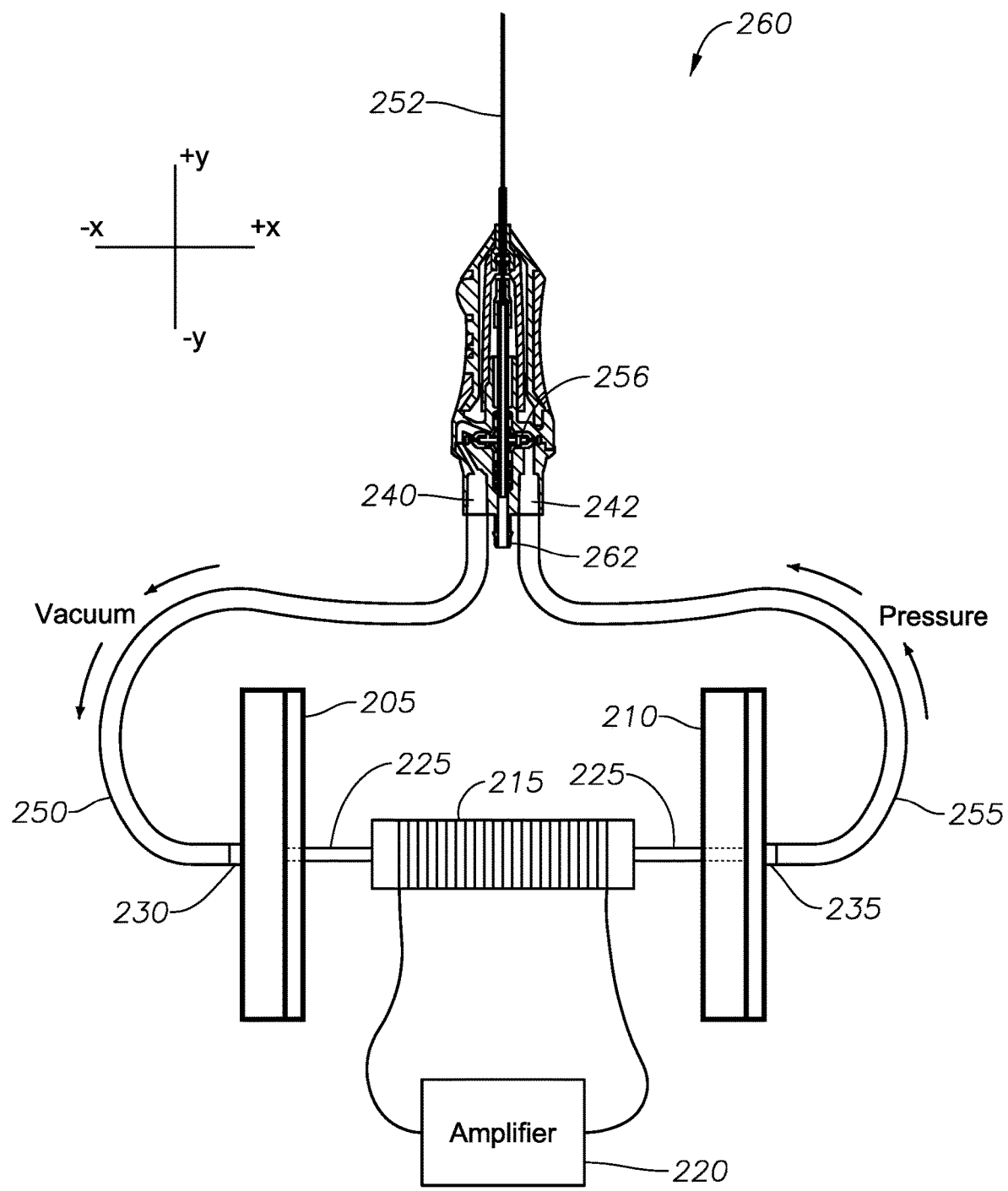
FIG. 5C illustrates a second portion of the pump cycle of a diaphragm pump driver system.

As shown in FIG. 5C, in a second portion of the pump cycle, the amplifier 220 will provide a current that causes the voice coil 215 to drive the shaft 225 and the diaphragm pump 210 in the +x direction, thereby pushing pressure through the air hose 255 and causing a negative displacement (−y) of the vitreous cutter diaphragm 256. The displacement of the shaft 225 in the +x direction will also pull the diaphragm pump 205, thereby pulling a vacuum in air hose 250 and further causing negative displacement (−y) of the vitreous cutter diaphragm 256 since the port 240 is in fluid communication with the −y side of the vitreous cutter diaphragm 256.

According to some embodiments of the present technology, the two pumps 205, 210 working 180° out of phase the vitreous cutter is more efficient than a positive pressure only drive system due to the addition of negative pressure acting on the vitreous cutter diaphragm rather than just venting the pressure as occurs in the open system. In some cases, the two pumps contain a pump diaphragm ranging between two and five times the size of the diaphragm in an ophthalmic surgical handpiece.

In some embodiments, a pressure sensor a feedback control system can be used to create a precise pressure profile. For example, this type of feedback system can be made to compensate for changes in temperature as well as atmospheric pressure. It may also be possible to account for variations in the hose characteristics including the hose length. In some cases, an initial pressure is made high, and then dropped to a lower pressure once the vitreous cutter has started moving. The pressure drop caused by the pneumatic hose compliance could be partially compensated.

Figure 6A:
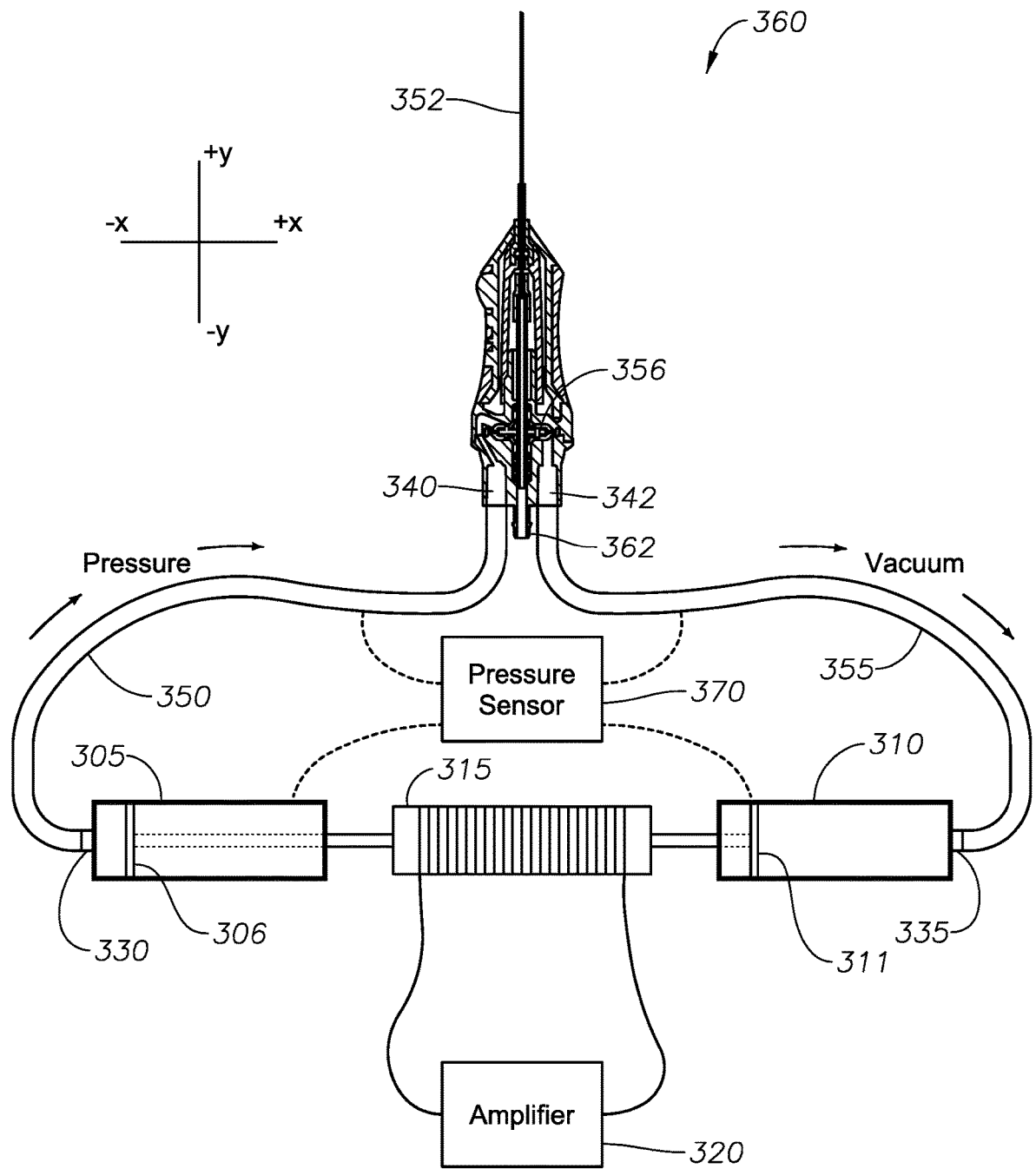
FIG. 6A illustrates a closed pneumatic piston driver system and a pressure sensor feedback control system.

FIG. 6A illustrates a closed pneumatic piston driver system 300 coupled with a hand piece 360 with ports 340, 342 that communicate fluid pressure to one side of a pneumatic driver diaphragm 356 which drives the inner cutting tube within an outer cutting tube 352. The hand piece can also include a suction port 362 to provide aspiration of materials from the cutter through an additional tube (not shown).

The closed pneumatic piston driver system 300 has a pair of pneumatic pistons 305, 310, a voice coil 315 and an amplifier 320. The voice coil 315 can include a shaft 325 coupled with piston rings 306, 311 in each of the pistons 305, 310. The amplifier 320 can drive the voice coil driver 315 with an alternating current, causing the shaft 325 to move back and forth and alternatively pumping one of the pistons 305, 310 to create positive pressure and pulling the other piston 305, 310 to pull negative pressure. The pistons 305, 310 can each include an outlet 330, 335 for coupling with an air hose 350, 355 and the ports 340, 342 of a hand piece 360.

FIG. 6A also illustrates a pressure sensor 370 coupled to one or more of the air hoses 350, 355, pneumatic pistons 305, 310, or other substantially hermetically sealed portions of the closed system. The pressure sensor 370 can be a part of a pressure sensor a feedback control system that can be used to create a precise pressure profile. For example, the pressure sensor 370 can be communicatively coupled with a controller (not shown) that can receive pressure data from the pressure sensor 370 and control the amplifier 320. For example, the controller can use pressure data to: compensate for changes in temperature as well as atmospheric pressure, to account for variations in the hose characteristics including the hose length, to set an initial pressure to a high setting and subsequently dropped to a lower pressure once the vitreous cutter has started moving, etc.

In some cases, the controller is communicatively coupled with the amplifier 320 and the controller can control the amplifier 320 based, at least in part, by the pressure data from the pressure sensor 370. For example, a pulse-width modulation signal or an output from a switching amplifier (e.g. Class-D amplifier) can be used to control the amplifier 320. In some cases, a digital to analog converter can drive the amplifier.

Also, some embodiments can involve a closed loop control system that can take feedback from the pressure sensor or some other part of the system other than just pressure from the tubing set. For example, some cases involve controlling the displacement of the voice coil with a position sensor, accelerometer, servomechanism, etc.

The pneumatic drivers for push/pull driving of a diaphragm in an ophthalmic surgical handpiece described in FIGS. 5A-6A illustrate two pneumatic pumps positioned coaxially on opposite sides of the voice coil and having a master/replica relationship where one pump generates positive pressure and one pump pulls negative pressure when the shaft of the voice coil driver is driven in a first direction, and vice versa. In some embodiments, a single pneumatic driver generates both positive and negative pressure in the closed system.

Figure 6B:
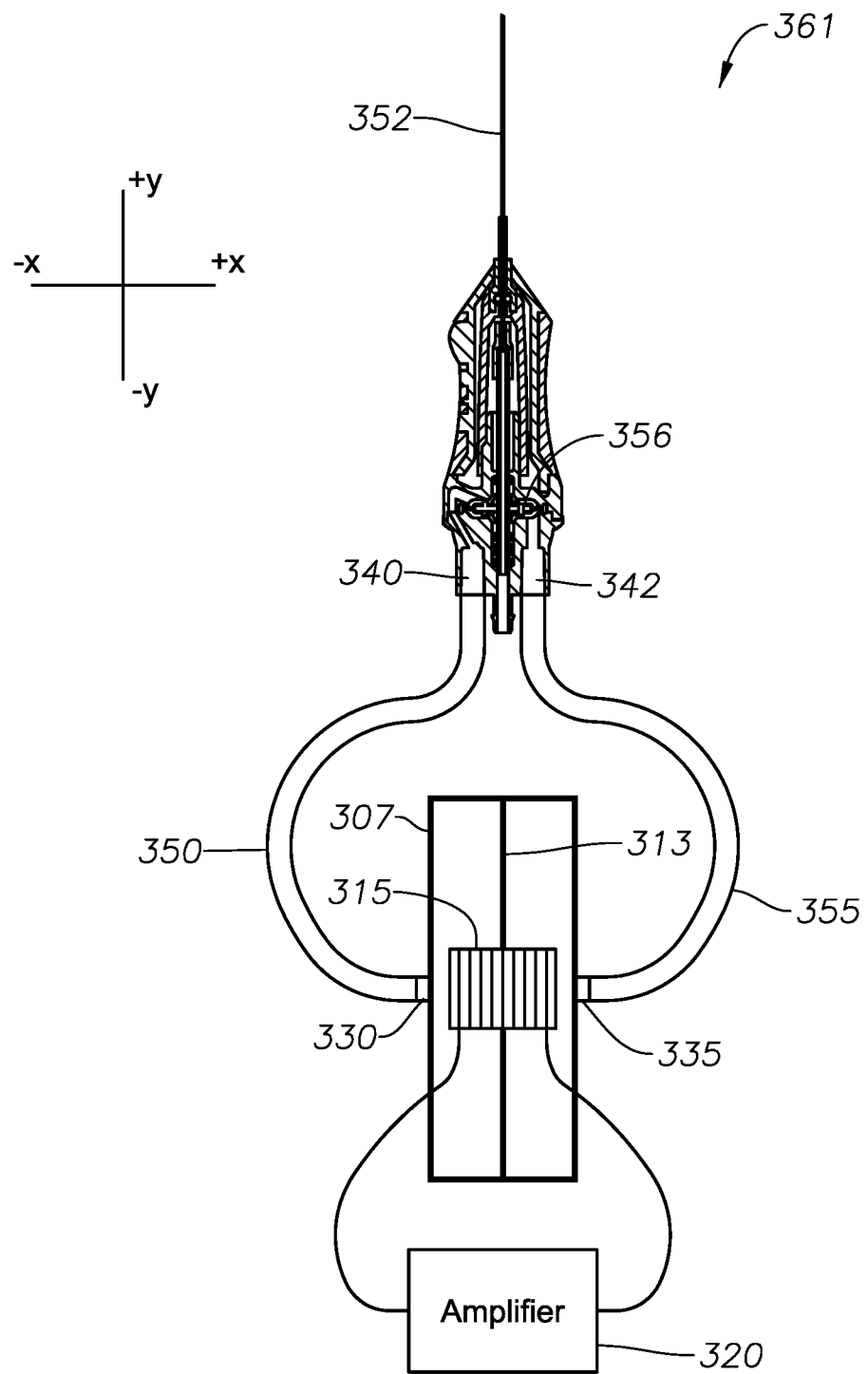
FIG. 6B illustrates a closed system with a voice coil contained within a single pneumatic pump.

FIG. 6B illustrates a closed system 361 with a voice coil contained within a single pneumatic pump 307 where the single pump 307 generates positive pressure and pulls negative pressure when the diaphragm 313 of the voice coil driver is driven in alternating directions.

Figure 7A:
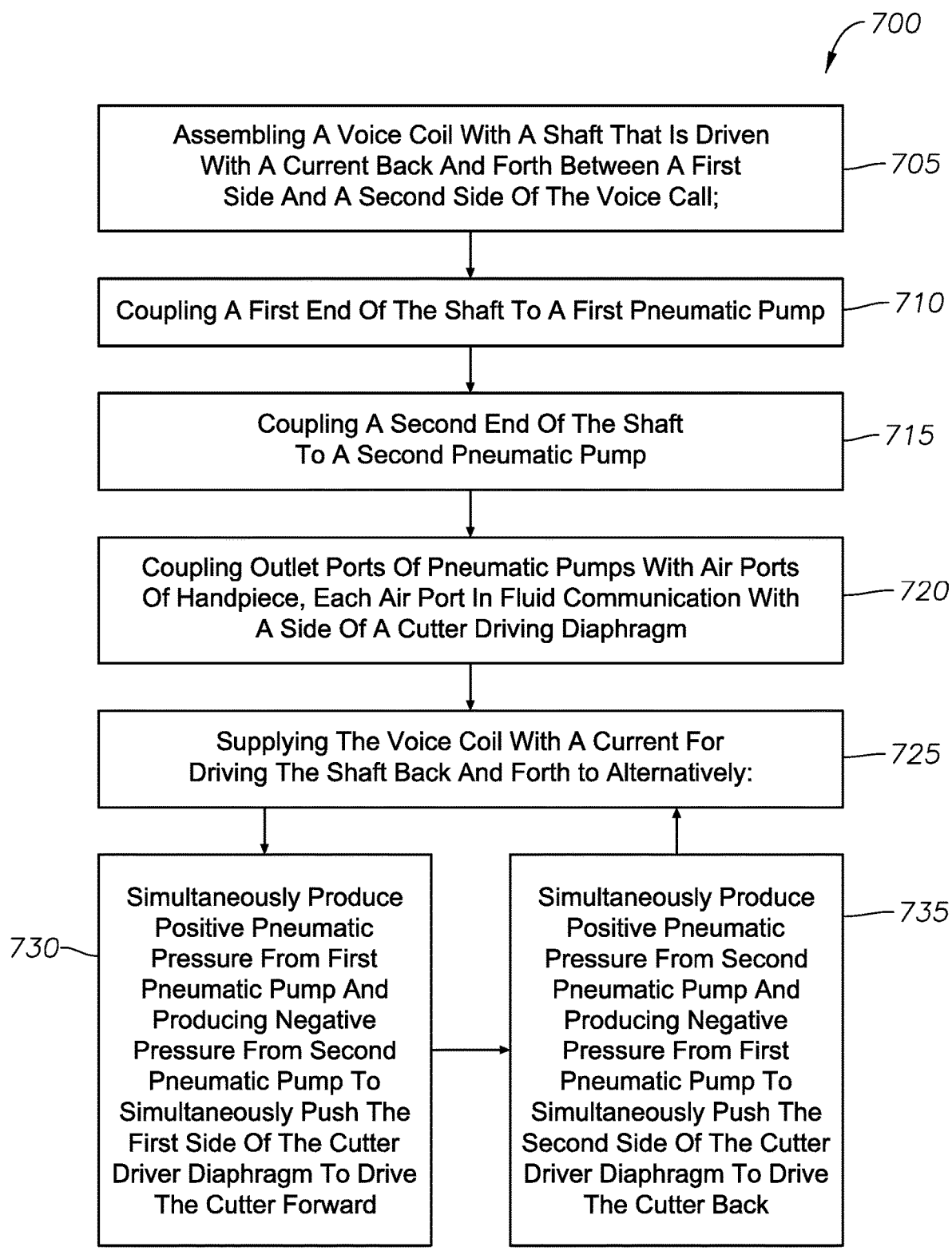
FIG. 7A illustrates a method of driving a vitrectomy cutter according to some embodiments of the present technology.

FIG. 7A illustrates a method 700 of driving a vitrectomy cutter according to some embodiments of the present technology. The method 700 can involve assembling a voice coil with a shaft that is driven with a current back and forth between a first side and a second side of the voice coil 705. Next, the method 700 involves coupling a first end of the shaft to a first pneumatic pump 710 and coupling a second end of the shaft to a second pneumatic pump 715. Also, the method 700 can involve coupling outlet ports of pneumatic pumps with air ports of handpiece, with each air port in fluid communication with a side of a cutter driving diaphragm 720.

Next, the method 700 can involve supplying the voice coil with a current for driving the shaft back and forth, thereby alternatively 725: simultaneously producing positive pneumatic pressure from the first pneumatic pump and producing negative pressure from the second pneumatic pump to simultaneously push the first side of the pneumatic driver diaphragm to drive the cutter forward 730; and simultaneously producing negative pneumatic pressure from the first pneumatic pump and producing positive pressure from the second pneumatic pump to simultaneously push the second side of the pneumatic driver diaphragm to drive the cutter back 735.

Figure 7B:
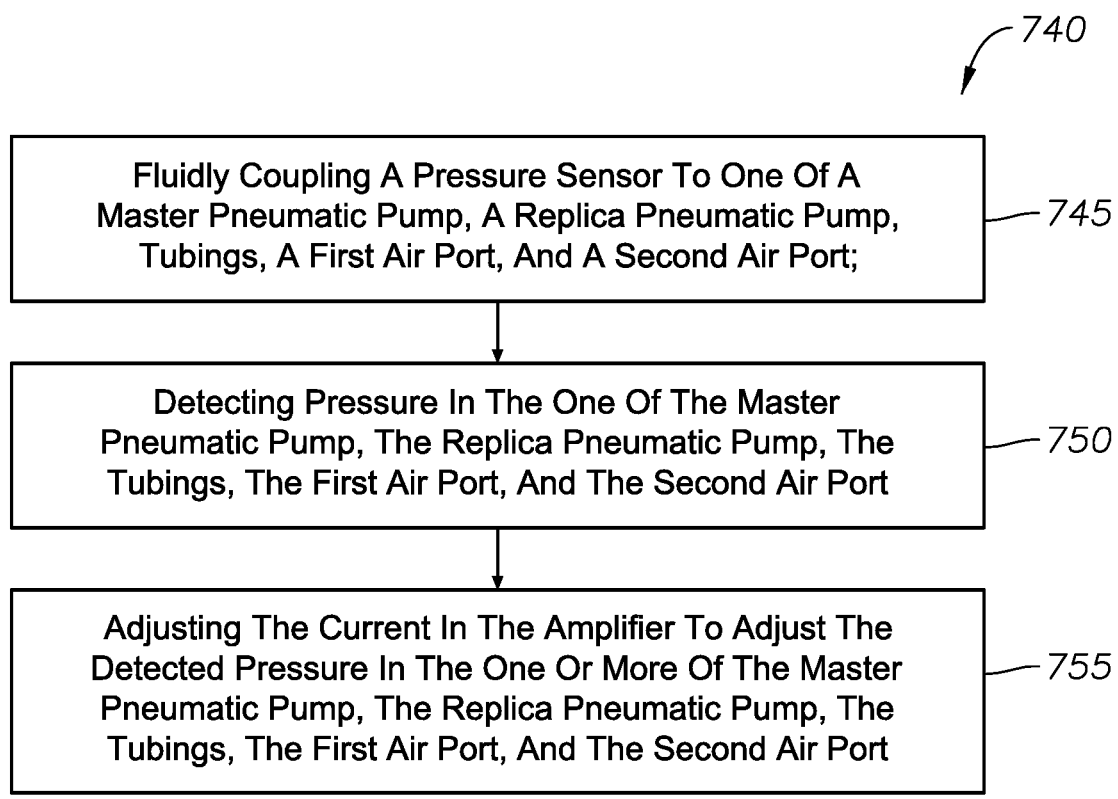
FIG. 7B illustrates a method of controlling pressure in a system for pneumatic driving of a surgical handpiece.

FIG. 7B illustrates a method 740 of controlling pressure in a system for pneumatic driving of a surgical handpiece according to some embodiments of the present technology. The method 740 can involve fluidly coupling a pressure sensor to one or more of the master pneumatic pump, the replica pneumatic pump, the tubings, the first air port, and the second air port 745. Next, the method 740 can involve detecting a pressure in the one or more of the master pneumatic pump, the replica pneumatic pump, the tubings, the first air port, and the second air port 750. Finally, the method 740 can involve adjusting the current in the amplifier to adjust the detected pressure in the one or more of the master pneumatic pump, the replica pneumatic pump, the tubings, the first air port, and the second air port 755.

Figure 8A:
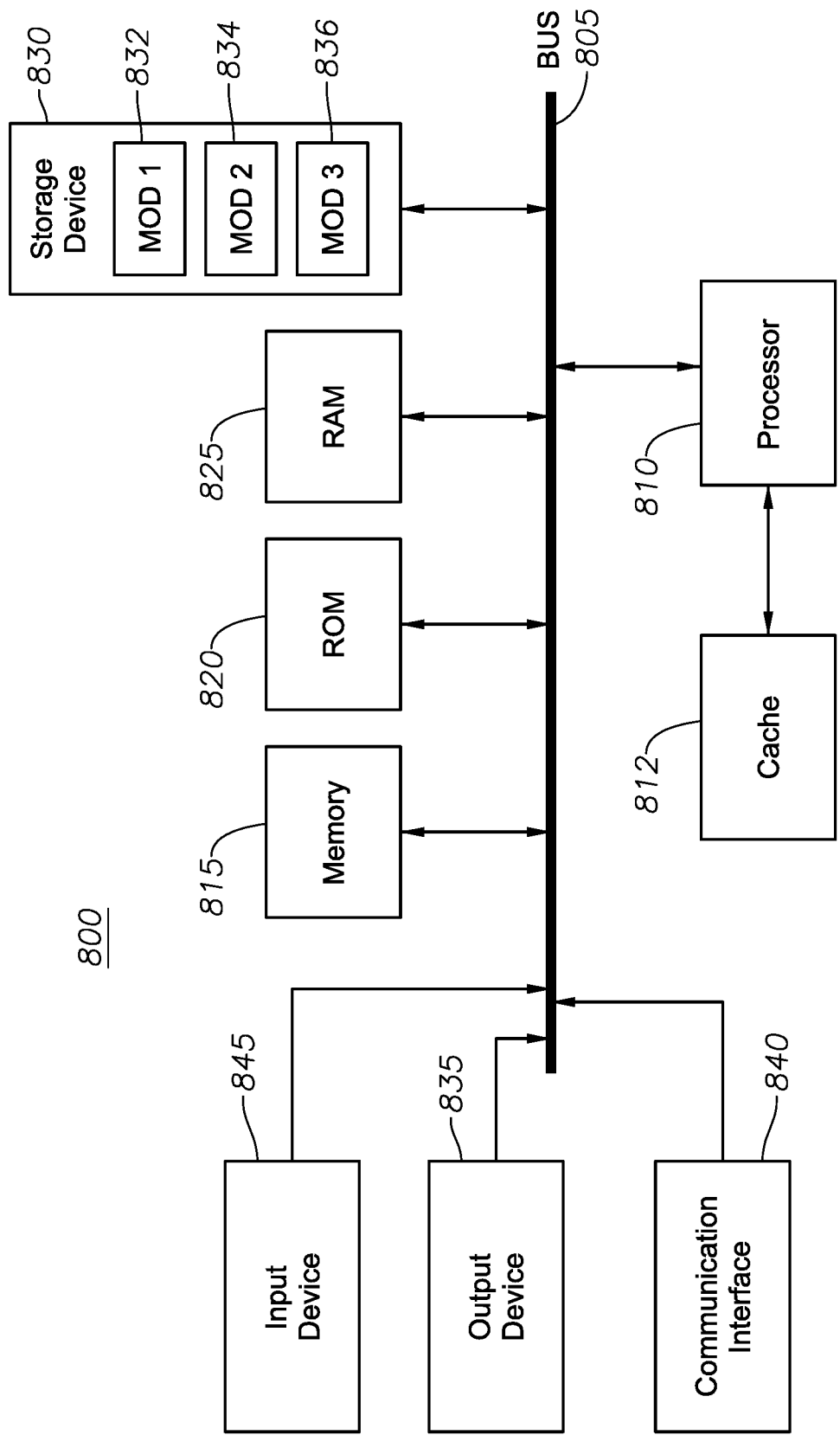
FIG. 8A and FIG. 8B illustrate exemplary possible system embodiments.
Figure 8B:
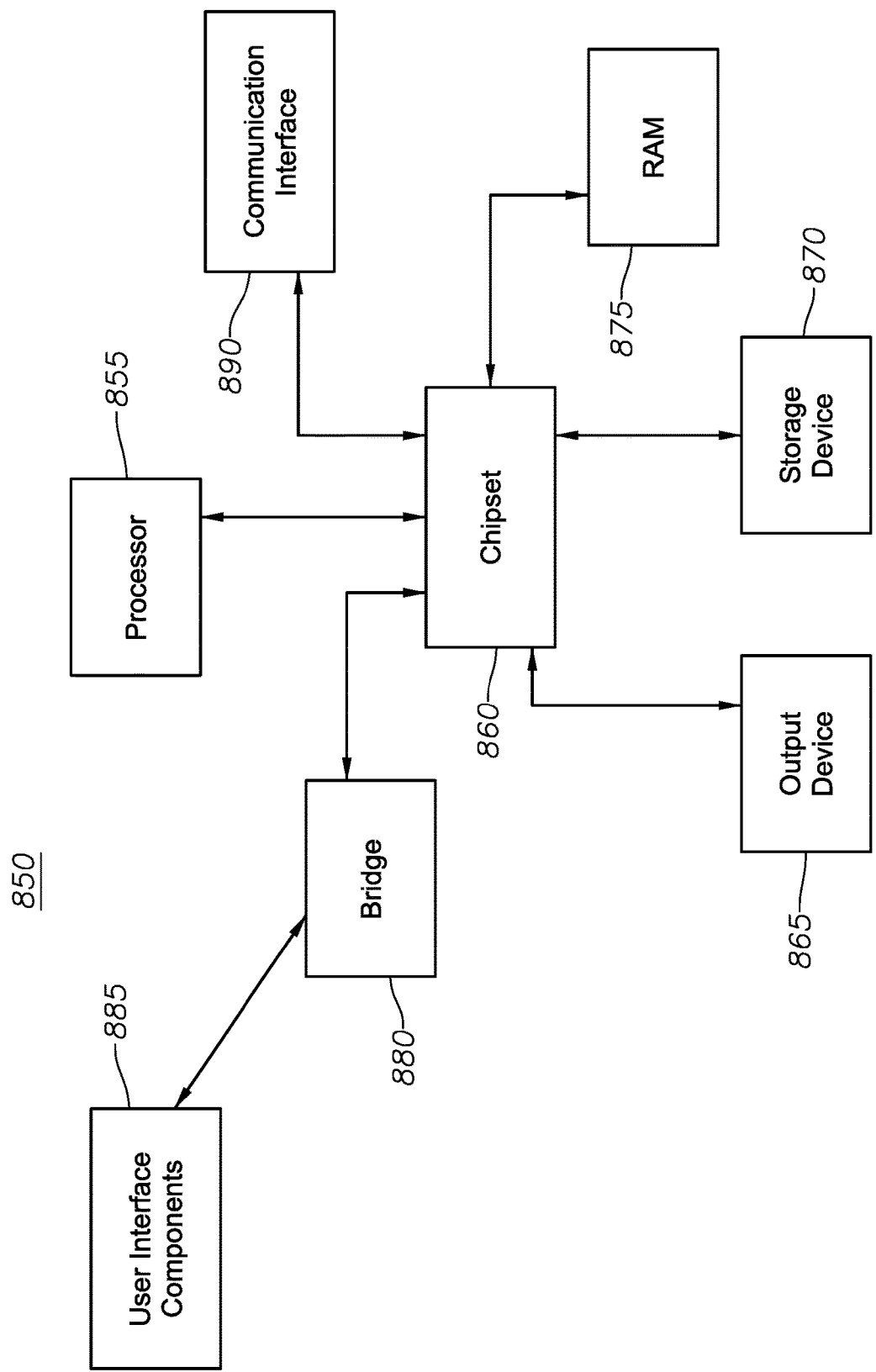

FIG. 8A and FIG. 8B illustrate exemplary possible system embodiments. The more appropriate embodiment will be apparent to those of ordinary skill in the art when practicing the present technology. Persons of ordinary skill in the art will also readily appreciate that other system embodiments are possible.

FIG. 8A illustrates a conventional system bus computing system architecture 800 wherein the components of the system are in electrical communication with each other using a bus 805. Exemplary system 800 includes a processing unit (central processing unit (CPU) or processor) 810 and a system bus 805 that couples various system components including the system memory 815, such as read only memory (ROM) 820 and random access memory (RAM) 825, to the processor 810. The system 800 can include a cache of high-speed memory connected directly with, in close proximity to, or integrated as part of the processor 810. The system 800 can copy data from the memory 815 and/or the storage device 830 to the cache 812 for quick access by the processor 810. In this way, the cache can provide a performance boost that avoids processor 810 delays while waiting for data. These and other modules can control or be configured to control the processor 810 to perform various actions. Other system memory 815 may be available for use as well. The memory 815 can include multiple different types of memory with different performance characteristics. The processor 810 can include any general purpose processor and a hardware module or software module, such as module 1 832, module 2 834, and module 3 836 stored in storage device 830, configured to control the processor 810 as well as a special-purpose processor where software instructions are incorporated into the actual processor design. The processor 810 may essentially be a completely self-contained computing system, containing multiple cores or processors, a bus, memory controller, cache, etc. A multi-core processor may be symmetric or asymmetric.

To enable user interaction with the computing device 500, an input device 845 can represent any number of input mechanisms, such as a microphone for speech, a touch-sensitive screen for gesture or graphical input, keyboard, mouse, motion input, speech and so forth. An output device 835 can also be one or more of a number of output mechanisms known to those of skill in the art. In some instances, multimodal systems can enable a user to provide multiple types of input to communicate with the computing device 800. The communications interface 840 can generally govern and manage the user input and system output. There is no restriction on operating on any particular hardware arrangement and therefore the basic features here may easily be substituted for improved hardware or firmware arrangements as they are developed.

Storage device 830 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 825, read only memory (ROM) 820, and hybrids thereof.

The storage device 830 can include software modules 832, 834, 836 for controlling the processor 810. Other hardware or software modules are contemplated. The storage device 830 can be connected to the system bus 805. In one aspect, a hardware module that performs a particular function can include the software component stored in a computer-readable medium in connection with the necessary hardware components, such as the processor 810, bus 805, display 835, and so forth, to carry out the function.

FIG. 8B illustrates a computer system 850 having a chipset architecture that can be used in executing the described method and generating and displaying a graphical user interface (GUI). Computer system 850 is an example of computer hardware, software, and firmware that can be used to implement the disclosed technology. System 850 can include a processor 855, representative of any number of physically and/or logically distinct resources capable of executing software, firmware, and hardware configured to perform identified computations. Processor 855 can communicate with a chipset 860 that can control input to and output from processor 855. In this example, chipset 860 outputs information to output 865, such as a display, and can read and write information to storage device 870, which can include magnetic media, and solid state media, for example. Chipset 860 can also read data from and write data to RAM 875. A bridge 880 for interfacing with a variety of user interface components 885 can be provided for interfacing with chipset 860. Such user interface components 885 can include a keyboard, a microphone, touch detection and processing circuitry, a pointing device, such as a mouse, and so on. In general, inputs to system 850 can come from any of a variety of sources, machine generated and/or human generated.

Chipset 860 can also interface with one or more communication interfaces 890 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 855 analyzing data stored in storage 870 or 875. Further, the machine can receive inputs from a user via user interface components 885 and execute appropriate functions, such as browsing functions by interpreting these inputs using processor 855.

It can be appreciated that exemplary systems 800 and 850 can have more than one processor 810 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A pneumatic driver for push/pull driving of a diaphragm in an ophthalmic surgical handpiece comprising:
    a voice coil driver including a voice coil and a shaft driven by the voice coil;
    a master pneumatic pump positioned on a first side of the voice coil driver and a replica pneumatic pump positioned on a second side of the voice coil driver, the master pneumatic pump and replica pneumatic pump each having:
        an outer body;
        an outlet; and
        an internal pump coupled with a driving arm coupled with the shaft of the voice coil driver such that a motion of the shaft in a first direction produces positive pressure by the master pneumatic pump and pulls negative pressure in the replica pneumatic pump and a motion of the shaft in a second direction produces positive pressure by the replica pneumatic pump and pulls negative pressure in the master pneumatic pump; and
    an amplifier configured to provide a current to the voice coil driver for driving the shaft back and forth in the first and the second direction.

2. The pneumatic driver of claim 1, wherein the replica pneumatic pump is positioned coaxially with the master pneumatic pump on the second side of the voice coil driver.

3. The pneumatic driver of claim 1, wherein the master pneumatic pump and the replica pneumatic pump each have a substantially hermetically sealed outer body.

4. The pneumatic driver of claim 1, wherein the internal pump of the master pneumatic pump and the replica pneumatic pump comprises a pump diaphragm ranging between two and five times the size of the diaphragm in an ophthalmic surgical handpiece.

5. The pneumatic driver of claim 1, wherein the internal pump of the master pneumatic pump and the replica pneumatic pump comprises a pneumatic piston having a piston ring coupled to the driving arm.

6. The pneumatic driver of claim 1, further comprising:
    a pair of tubings respectively coupled to an outlet tube port of the master pneumatic pump and the replica pneumatic pump,
    wherein the master pneumatic pump and the replica pneumatic pump produce and pull a pressure between five and fifteen pounds per square inch at a distal end of each respective tubing.

7. A surgical system comprising:
    a vitrectomy handpiece having a housing containing an inner cutting tube at least partially contained within an outer cutting tube and coupled with a pneumatic driver diaphragm, wherein a first side of the pneumatic driver diaphragm is in fluid communication with a first air port, and wherein a second side of the pneumatic driver diaphragm is in fluid communication with a second air port;
    a pneumatic driver for push/pull driving of a diaphragm in an ophthalmic surgical handpiece comprising:
    a voice coil driver including a voice coil and a shaft driven by the voice coil;
    a master pneumatic pump positioned on a first side of the voice coil driver and a replica pneumatic pump positioned on a second side of the voice coil driver, the master pneumatic pump and replica pneumatic pump each having:
        an outer body;
        an outlet; and
        an internal pump coupled with a driving arm coupled with the shaft of the voice coil driver such that a motion of the shaft in a first direction produces positive pressure by the master pneumatic pump and pulls negative pressure in the replica pneumatic pump and a motion of the shaft in a second direction produces positive pressure by the replica pneumatic pump and pulls negative pressure in the master pneumatic pump;
    an amplifier configured to provide a current to the voice coil driver for driving the shaft back and forth in the first and the second direction; and
    wherein the positive pneumatic pressure from the master pneumatic pump and the negative pressure from the replica pneumatic pump simultaneously pushes the first side of the pneumatic driver diaphragm to drive the inner cutting tube forward within the outer cutting tube, and
    wherein the positive pneumatic pressure from the replica pneumatic pump and the negative pressure from the master pneumatic pump simultaneously pushes the second side of the pneumatic driver diaphragm to drive the inner cutting tube back within the outer cutting tube.

8. The surgical system of claim 7, further comprising a pair of tubings respectively coupling an outlet tube port of the master pneumatic pump with the first air port of the vitrectomy handpiece and an outlet tube port of the replica pneumatic pump with the second air port of the vitrectomy handpiece.

9. The surgical system of claim 8, further comprising:
    a pressure sensor configured to detect a pressure in one or more of the master pneumatic pump, the replica pneumatic pump, the tubings, the first air port, and the second air port.

10. The surgical system of claim 8, further comprising:
a controller comprising a processor and non-transitory computer-readable medium containing instructions which, when executed by the processor, causes the controller to adjust the current in the amplifier to adjust the pressure in one or more of the master pneumatic pump, the replica pneumatic pump, the tubings, the first air port, and the second air port.

11. The surgical system of claim 7, wherein the replica pneumatic pump is positioned coaxially with the master pneumatic pump on the second side of the voice coil driver.

12. The surgical system of claim 7, wherein the master pneumatic pump and the replica pneumatic pump each have a substantially hermetically sealed outer body.

13. The surgical system of claim 7, wherein the outer cutting tube has a tissue receiving outer port at a distal end of the outer cutting tube.

14. The surgical system of claim 7, wherein the master pneumatic pump and the replica pneumatic pump each have an internal diaphragm, an outlet tube port on a first side of the internal diaphragm, and a shaft coupling on a second side of the internal diaphragm for coupling with the shaft.

15. The surgical system of claim 7, wherein the voice coil receives a current from the amplifier to alternatively:
drive the shaft to drive an internal diaphragm of the master pneumatic pump to push pneumatic pressure through an outlet tube port of the master pneumatic pump and retract an internal diaphragm of the replica pneumatic pump to pull a vacuum through an outlet tube port of the replica pneumatic pump; and
drive the shaft to drive the internal diaphragm of the replica pneumatic pump to push pneumatic pressure through the outlet tube port of the replica pneumatic pump and retract the internal diaphragm of the master pneumatic pump to pull a vacuum through the outlet tube port of the master pneumatic pump.

\* \* \* \* \*